United States Patent [19]

Latham

[11] 4,280,492
[45] Jul. 28, 1981

[54] TRACHEOSTOMY TUBE

[76] Inventor: Phillip B. Latham, 111 Conn Ter., Lexington, Ky. 40508

[21] Appl. No.: 82,327

[22] Filed: Oct. 5, 1979

[51] Int. Cl.³ .................... A61M 16/00; A61M 25/00
[52] U.S. Cl. ........................... 128/207.15; 128/207.16
[58] Field of Search ...................... 128/207.14, 207.15, 128/207.16, 204.18, 349 B, 349 BV

[56] References Cited
U.S. PATENT DOCUMENTS

| 3,504,676 | 4/1970 | Lomholt | 128/207.15 |
| 3,529,596 | 9/1970 | Garner | 128/207.15 X |
| 4,037,605 | 7/1977 | Firth | 128/207.15 |

FOREIGN PATENT DOCUMENTS 1248230  8/1967  Fed. Rep. of Germany ...... 128/207.15

Primary Examiner—Henry J. Recla
Attorney, Agent, or Firm—Birch, Stewart, Kolasch & Birch

[57] ABSTRACT

An apparatus and device for permitting a person with a tracheostomy to speak while being ventilated. A tracheostomy tube having an orifice in its tubular wall and a valve means in operative association with the orifice are provided. A valve controlling means is arranged to cause the valve means to block the orifice when a ventilator which is connected to the tracheostomy tube feeds inhalation oxygen thereto, and to open the orifice when exhalation occurs, thereby allowing exhaled breath to flow upwardly in the trachea past the larynx to permit speech. The valve means may comprise a balloon mounted inside of a hood.

8 Claims, 4 Drawing Figures

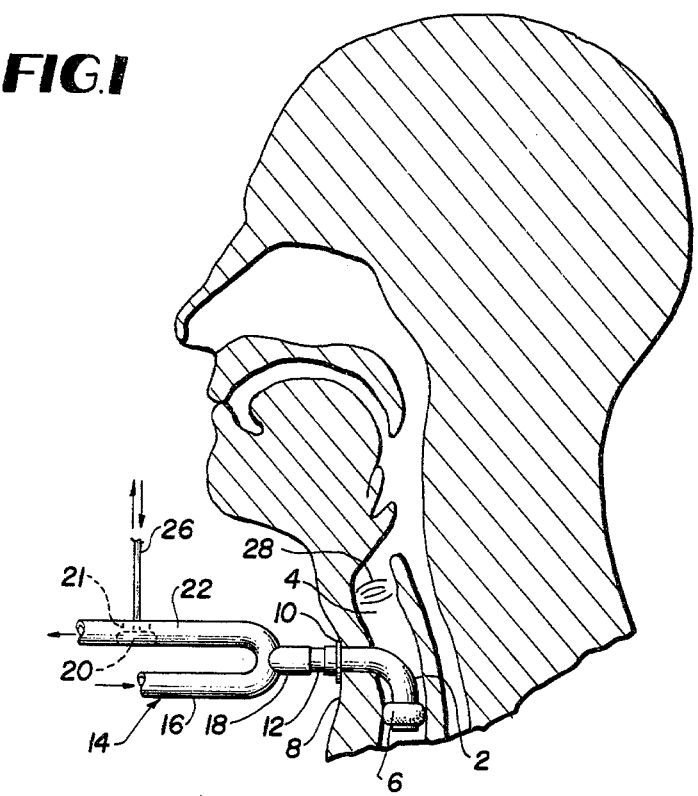

TRACHEOSTOMY TUBE

BACKGROUND OF THE INVENTION

The present invention is directed to an apparatus and device for allowing a person with a tracheostomy to speak while being ventilated.

Ventilators are frequently employed in hospitals to help the breathing of patients who have had tracheostomies. The ventilator supplies air or oxygen to the tracheostomy tube under positive pressure at periodic intervals and is arranged to allow exhalation of breath at intervening intervals.

While the ventilator serves an extremely useful function, patients who are on ventilators are ordinarily not able to speak. This is because substantially all of the breath which is exhaled by the patient passes out the tracheostomy tube and into the ventilator, and no breath passes up the trachea and past the larynx, which is a necessary condition for speech. This problem is compounded by the fact that patients on ventilators frequently have other enfeebling conditions which make it difficult or impossible for them to communicate by physical means other than speaking.

One approach of the prior art to this problem has been to provide an apparatus having two conduits, one for supplying air for breathing and the other for supplying air to the vicinity of the larynx for speaking. However, use of this apparatus does not allow the patient to use his own breath in the speaking process.

Additionally, the prior art is replete with devices for allowing a person with a tracheostomy but not on a ventilator to speak. These typically involve the use of a one-way valve at the throat end of the tracheostomy tube, and are not suitable for use in conjunction with ventilators.

SUMMARY OF THE INVENTION

It is therefore an object of the invention to provide an apparatus and device for allowing a person with a tracheostomy to speak while being ventilated.

It is a further object to provide such an apparatus which allows the person's own exhaled breath to flow past his larynx to cause the speech.

It is still a further object of the invention to provide an apparatus which is relatively simple and inexpensive to manufacture, and which is safe to use.

The above objects are accomplished by providing a tracheostomy tube having an orifice in its tubular wall and a valve means in operative association with the orifice for selectively providing and preventing egress. Additionally, a valve controlling means is provided which controls the valve means to prevent egress from the tracheostomy tube into the trachea when the ventilator feeds oxygen under positive pressure and inhalation occurs, and to provide egress from the tracheostomy tube into the trachea when exhalation occurs. The exhaled breath flows upwardly in the trachea past the larynx to permit speech.

In the preferred embodiment, the valve means is an inflatable valve comprised of a balloon and a hood.

BRIEF DESCRIPTION OF THE DRAWINGS

The invention will be better understood by referring to the accompanying drawings in which:

FIG. 1 is a pictorial illustration of conventional apparatus in which a ventilator is connected to a tracheostomy tube.

FIG. 2 is a pictorial illustration of an embodiment of the present invention.

FIGS. 3 and 4 are cross-sectional detailed views of the balloon and hood structure of the embodiment of FIG. 2

DESCRIPTION OF CERTAIN PREFERRED EMBODIMENTS

Referring to FIG. 1, curved tracheostomy tube 2 is shown inserted in the trachea 4 of a patient who has been operated on. The tube is typically made of plastic and its lower end is seated in the trachea by inflatable donut 6 which is made of expandable, flexible material, and which is maintained in the inflated state while the tracheostomy tube is inserted. The upper end of the tube is seated at the outside of the throat 8 by flange 10, and a rigid termination portion 12 of the tube extends a short distance beyond the flange. Such a tracheostomy tube is conventional and is ordinarily utilized in cases where due to an obstruction or for other reasons, the person experiences difficulty in breathing through his or her own anatomy.

In some cases the tracheostomy tube 2 may be comprised of outer and inner cannulas. If such a configuration is used, the outer cannula is as shown, and an inner cannula is slidably insertable therein. The inner cannula may be removed to empty secretions and/or other accumulated material without disturbing the position in the trachea of the outer cannula.

Ventilator 14 is connected to the tracheostomy tube for providing air or oxygen under positive pressure to the tube and thus to the trachea. The ventilator is comprised of a structure which includes U-shaped conduit 16 having a straight tubular portion 18 projecting therefrom. An inflatable valve 20, which may be a balloon attached to a manifold 21 or other conventional structure, is disposed in upper leg 22 of U-shaped conduit 16, and tubular extension 18 telescopes onto tracheostomy tube termination 12, where it is retained by friction.

At periodic intervals, a source (not shown) feeds air or oxygen under positive pressure into the lower leg of U-shaped conduit 16, while air is simultaneously fed through conduit 26 into balloon 20. This inflates the balloon, thus closing upper leg 22, and causing substantially all of the air or oxygen under pressure to flow into the tracheostomy tube and thus into the trachea. When the patient exhales, the apparatus is arranged to deflate balloon 20 so that the exhaled breath may flow out upper leg 22. The structure and operation of ventilator 14 is conventional and forms no part of the present invention.

The problem with the above-described apparatus is that during the time that it is deployed the patient cannot speak. For speech to be possible, a stream of breath must be directed past the larynx 28. With the apparatus of FIG. 1, substantially all exhaled breath flows out of the tracheostomy tube 2 into the ventilator, while substantially no breath flows upwardly past the larynx.

The apparatus of the present invention allows a stream of breath to be projected upwardly in the trachea during exhalation. Referring to FIG. 2, wherein like numerals identify the same parts as in FIG. 1, it is seen that tracheostomy tube 2 has an orifice 30 in its tubular sidewall, and that valve means 32 and tubing 44 have been added to the apparatus, which otherwise is the same as shown in FIG. 1.

The valve means 32 is operatively associated with the orifice 30, and is arranged to block the orifice during inhalation and to open it during exhalation to project a stream of breath upwardly into the trachea to permit speech. In the preferred embodiment valve means 32 is comprised of the combination of inflatable and deflatable balloon 34 and cup-shaped hood 36.

Hood 36 encloses the balloon and is shaped to fit over tube 2' as is shown in FIGS. 2, 3, and 4. If desired, as a positioning aid, the bottom of the hood may be arranged to abut inflatable donut 6'. Additionally, the hood has one or more openings 38 in the top thereof which provide access to the trachea. Conduits 40 and 44 connect balloon 34 to the same source of air which controls balloon 20' of the ventilator. Conduit 44 enters the hood through opening 43, which may be sealed around conduit 44 so as to be leak-proof.

In the operation of the apparatus, when the ventilator feeds air or oxygen under positive pressure into the lower leg of U-shaped conduit 16', air is simultaneously fed through conduits 40, 42, and 44 to inflate balloons 20' and 34. As in the apparatus of FIG. 1, balloon 20' blocks the upper leg 22' of the U-shaped conduit and thus causes the air or oxygen under pressure to flow into the tracheostomy tube 2'. Since balloon 34 is also inflated, it blocks both orifices 30 and 38 as shown in FIGS. 2 and 3, thus preventing egress from tracheostomy tube 2' and causing all of the air or oxygen which entered the tube to flow through the entire length of it and to be inhaled into the patient's trachea.

On the other hand, when exhalation occurs, balloons 20' and 34 become deflated. Deflation of balloon 34 unblocks orifices 30 and 38 and provides a path connecting the orifices inside of the hood, as shown in FIG. 4. Thus, exhaled breath flows upwardly through orifices 30 and 38, and into the trachea past the larynx to permit speech.

In a further embodiment of the invention, tracheostomy tube 2' is comprised of outer and inner cannulas, with the inner cannula being slidably insertable into the outer. In this case, the cannulas would have coincident orifices 30, so that breath can be expelled into the trachea, as in FIG. 2. An advantage of the embodiment using two cannulas is that if the balloon in the hood ruptures or if other problems that impair positive pressure breathing develop, the inner cannula with the orifice can be replaced with the standard inner cannula, and the apparatus will function as in FIG. 1.

Thus, an apparatus for permitting speech while being ventilated has been disclosed. It is relatively simple, inexpensive to manufacture, and safe to use. While I have described certain embodiments of my invention, I wish it to be understood that I do not intend to be restricted thereto, but rather intend to cover all variations, modifications and uses which come within the spirit of the invention, which is limited only to the claims appended hereto.

I claim:

1. An apparatus for allowing a person with a tracheostomy to speak while being ventilated comprising,
a curved tracheostomy tube for insertion into the trachea beneath the larynx, said tube having first and second open ends and also having an orifice in its tubular wall in a position which resides inside the trachea when the tube is inserted with the first open end extending to the outside of the throat,
valve means associated with said orifice for selectively providing and preventing egress from it,
ventilator apparatus including cycling means for periodically feeding oxygen under positive pressure into said first open end of said tracheostomy tube and for periodically allowing exhalation of breath, and
means responsive to the cycling of said ventilator apparatus for controlling said valve means for preventing egress from said orifice when said oxygen is fed under positive pressure and for providing egress from said orifice when said exhalation occurs, whereby exhaled breath enters the trachea and rises therein past the larynx to allow speech.

2. The apparatus of claim 1 wherein said orifice in said tracheostomy tube is disposed in a portion of said tubular wall which faces towards said larynx when the tube is inserted.

3. The apparatus of claim 2 wherein said valve means comprises first inflatable and deflatable means disposed in proximity to said orifice, and wherein said means for controlling said valve means inflates said inflatable and deflatable means to cover said orifice to prevent said egress and deflates said inflatable and deflatable means to uncover said orifice to provide said egress.

4. The apparatus of claim 3 wherein said inflatable and deflatable means is disposed in a hood which covers a portion of said tracheostomy tube, said hood having at least one opening in it for providing egress to the trachea, and said inflatable and deflatable means covering said opening as well as said orifice when inflated and uncovering said opening as well as said orifice when deflated.

5. The apparatus of claim 3 wherein said ventilator apparatus includes separate oxygen feeding and egress tubes intersecting near and attached to said first open end of said tracheostomy tube, second inflatable and deflatable means being located in said egress tube, said apparatus further including means for inflating said second means when said oxygen is fed under positive pressure and for deflating it when exhalation occurs.

6. The apparatus of claim 5 wherein said means for controlling said valve means and said means for inflating and deflating said second inflatable and deflatable means includes a common periodically controlled pressure source means and a common conduit.

7. The apparatus of claim 3 further including a donut shaped inflatable mounting means located near said second open end of said tracheostomy tube for mounting said tracheostomy tube in the trachea.

8. A device which when connected to a ventilator means will allow a person with a tracheostomy to speak while being ventilated comprising,
a curved tracheostomy tube for insertion into the trachea beneath the larynx, said tube having first and second open ends and also having an orifice in its tubular wall in a position which resides inside the trachea when the tube is inserted with the first open end extending to the outside of the throat,
valve means associated with said orifice for selectively providing and preventing egress from it,
said first end of said tracheostomy tube being adapted for connection to a ventilator apparatus which includes cycling means for periodically feeding oxygen under positive pressure into said first end when connected and for periodically allowing exhalation of breath, and means adapted to be connected to said cycling means and responsive thereto for controlling said valve means for preventing egress from said orifice when said ventilator means feeds oxygen under positive pressure and for providing egress from said orifice when said exhalation occurs, whereby exhaled breath enters the trachea and rises therein past the larynx to allow speech.

* * * * *